United States Patent [19]
Kelly et al.

[11] Patent Number: 4,992,378
[45] Date of Patent: Feb. 12, 1991

[54] C-DNA ENCODING HUMAN PROLACTIN RECEPTOR

[75] Inventors: Paul A. Kelly, Quebec, Canada; Jean Djiane, Fontenay-aux-Roses, France

[73] Assignee: The Royal Institution for the Advancement of Learning (McGill University), Montreal, Canada

[21] Appl. No.: 286,445

[22] Filed: Dec. 16, 1988

[51] Int. Cl.$^5$ .................. C12N 15/12; C12N 15/70
[52] U.S. Cl. ............................ 435/320.1; 435/69.1; 435/172.3; 536/27
[58] Field of Search ................ 536/27; 435/68, 320, 435/172.3; 935/23, 27, 70, 71

[56] References Cited
PUBLICATIONS

Murphy et al., J. Biol. Chem., vol. 262(31), pp. 15236–15241 (1987).
Katoh et al., Chemical Abstracts, vol. 103, #17158a (1985).
Ellis et al., Cell, vol. 45, pp. 721–732 (1986).
Murphy et al., J. Biol. Chem., vol. 263(5), pp. 2397–2401 (1988).
Boutin et al., Cell, vol. 53, pp. 69–77 (1988).

Primary Examiner—Richard A. Schwartz
Attorney, Agent, or Firm—Dressler, Goldsmith, Shore, Sutker & Milnamow, Ltd.

[57] ABSTRACT

Isolation and cloning of the cDNA sequence of the human prolactin receptor and the development of the cDNA sequence in a plasmid vector capable of transforming cell lines that will produce the human prolactin receptor.

3 Claims, 8 Drawing Sheets

```
-284     GGAGGCTGAAATCCCCAGACGCCGGTTTTCTGGGCTGGGCT
-243 TTCTGCTTACTCACTCCTTCTCCCTCTTTCTGGATTTTACCGACC
-198 GTTCGCGAAACAGCTTTCCACACAATGGAGCTTCATGTCCTCGTG
-153 CAGGAAGTACTCATCGACTGATGTGGCAGACTTTGCTCCCTGACA
-108 AAACTAAAGAACTCTCCTATTCATGGAGGCGAACACTGAGGATGC
 -63 TTTCCACATGAACCCTGAAGTGAACTTCTGATACATTTCCTGCAG
 -18 CAAGAGAAGGCAGCCAACATGAAGGAAAATGTGGCATCTGCAACC
                              M   K   E   N   V   A   S   A   T
                             -24                 -20

28 GTTTTCACTCTGCTACTTTTTCTCAACACCTGCCTTCTGAATGGA
      V   F   T   L   L   L   F   L   N   T   C   L   L   N   G
                 -10                  -5

73 CAGTTACCTCCTGGAAAACCTGAGATCTTTAAATGTCGTTCTCCC
      Q   L   P   P   G   K   P   E   I   F   K   C   R   S   P
                      5                  10                  15

118 AATAAGGAAACATTCACCTGCTGGTGGAGGCCTGGGACAGATGGA
      N   K   E   T   F   T   C   W   W   R   P   G   T   D   G
                     20                  25                  30

163 GGACTTCCTACCAATTATTCACTGACTTACCACAGGGAAGGAGAG
      G   L   P   T   N   Y   S   L   T   Y   H   R   E   G   E
                     35                  40                  45

208 ACACTCATGCATGAATGTCCAGACTACATAACCGGTGGCCCCAAC
      T   L   M   H   E   C   P   D   Y   I   T   G   G   P   N
                     50                  55                  60

253 TCCTGCCACTTTGGCAAGCAGTACACCTCCATGTGGAGGACATAC
      S   C   H   F   G   K   Q   Y   T   S   M   W   R   T   Y
                     65                  70                  75

298 ATCATGATGGTCAATGCCACTAACCAGATGGGAAGCAGTTTCTCG
      I   M   M   V   N   A   T   N   Q   M   G   S   S   F   S
                     80                  85                  90
```

FIG. 1A

```
343 GATGAACTTTATGTGGACGTGACTTACATAGTTCAGCCAGACCCT
     D   E   L   Y   V   D   V   T   Y   I   V   Q   P   D   P
                    95              100             105

388 CCTTTGGAGCTGGCTGTGGAAGTAAAACAGCCAGAAGACAGAAAA
     P   L   E   L   A   V   E   V   K   Q   P   E   D   R   K
                    110             115             120

433 CCCTACCTGTGGATTAAATGGTCTCCACCTACCCTGATTGACTTA
     P   Y   L   W   I   K   W   S   P   P   T   L   I   D   L
                    125             130             135

478 AAAACTGGTTGGTTCACGCTCCTGTATGAAATTCGATTAAAACCC
     K   T   G   W   F   T   L   L   Y   E   I   R   L   K   P
                    140             145             150

523 GAGAAAGCAGCTGAGTGGGAGATCCATTTTGCTGGGCAGCAAACA
     E   K   A   A   E   W   E   I   H   F   A   G   Q   Q   T
                    155             160             165

568 GAGTTTAAGATTCTCAGCCTACATCCAGGACAGAAATACCTTGTC
     E   F   K   I   L   S   L   H   P   G   Q   K   Y   L   V
                    170             175             180

613 CAGGTTCGCTGCAAACCAGACCATGGATACTGGAGTGCATGGAGT
     Q   V   R   C   K   P   D   H   G   Y   W   S   A   W   S
                    185             190             195

658 CCAGCGACCTTCATTCAGATACCTAGTGACTTCACCATGAATGAT
     P   A   T   F   I   Q   I   P   S   D   F   T   M   N   D
                    200             205             210

703 ACAACCGTGTGGATCTCTGTGGCTGTCCTTTCTGCTGTCATCTGT
     T   T   V   W   I   S   V   A   V   L   S   A   V   I   C
                    215             220             225

748 TTGATTATTGTCTGGGCAGTGGCTTTGAAGGGCTATAGCATGGTG
     L   I   I   V   W   A   V   A   L   K   G   Y   S   M   V
                    230             235             240
```

FIG. 1B

```
 793 ACCTGCATCTTTCCGCCAGTTCCTGGGCCAAAAATAAAAGGATTT
      T  C  I  F  P  P  V  P  G  P  K  I  K  G  F
                      245         250           255

838 GATGCTCATCTGTTGGAGAAGGGCAAGTCTGAAGAACTACTGAGT
      D  A  H  L  L  E  K  G  K  S  E  E  L  L  S
                260           265            270

883 GCCTTGGGATGCCAAGACTTTCCTCCCACTTCTGACTATGAGGAC
      A  L  G  C  Q  D  F  P  P  T  S  D  Y  E  D
                  275            280         285

928 TTGCTGGTGGAGTATTTAGAAGTAGATGATAGTGAGGACCAGCAT
      L  L  V  E  Y  L  E  V  D  D  S  E  D  Q  H
                   290         295            300

973 CTAATGTCAGTCCATTCAAAAGAACACCCAAGTCAAGGTATGAAA
      L  M  S  V  H  S  K  E  H  P  S  Q  G  M  K
                  305           310           315

1018 CCCACATACCTGGATCCTGACACTGACTCAGGCCGGGGGAGCTGT
      P  T  Y  L  D  P  D  T  D  S  G  R  G  S  C
                320            325           330

1063 GACAGCCCTTCCCTTTTGTCTGAAAAGTGTGAGGAACCCCAGGCC
      D  S  P  S  L  L  S  E  K  C  E  E  P  Q  A
                 335           340            345

1108 AATCCCTCCACATTCTATGATCCTGAGGTCATTGAGAAGCCAGAG
      N  P  S  T  F  Y  D  P  E  V  I  E  K  P  E
                    350         355            360

1153 AATCCTGAAACAACCCACACCTGGGACCCCCAGTGCATAAGCATG
      N  P  E  T  T  H  T  W  D  P  Q  C  I  S  M
                 365           370            375

1198 GAAGGCAAAATCCCCTATTTTCATGCTGGTGGATCCAAATGTTCA
      E  G  K  I  P  Y  F  H  A  G  G  S  K  C  S
                   380           385           390
```

FIG. 1C

1243 ACATGGCCCTTACCACAGCCCAGCCAGCACAACCCCAGATCCTCT
   T  W  P  L  P  Q  P  S  Q  H  N  P  R  S  S
    395     400     405

1288 TACCACAATATTACTGATGTGTGTGAGCTGGCTGTGGGCCCTGCA
   Y  H  N  I  T  D  V  C  E  L  A  V  G  P  A
    410     415     420

1333 GGTGCACCGGCCACTCTGTTGAATGAAGCAGGTAAAGATGCTTTA
   G  A  P  A  T  L  L  N  E  A  G  K  D  A  L
    425     430     435

1378 AAATCCTCTCAAACCATTAAGTCTAGAGAAGAGGGAAAGGCAACC
   K  S  S  Q  T  I  K  S  R  E  E  G  K  A  T
    440     445     450

1423 CAGCAGAGGGAGGTAGAAAGCTTCCATTCTGAGACTGACCAGGAT
   Q  Q  R  E  V  E  S  F  H  S  E  T  D  Q  D
    455     460     465

1468 ACGCCCTGGCTGCTGCCCCAGGAGAAAACCCCCTTTGGCTCCGCT
   T  P  W  L  L  P  Q  E  K  T  P  F  G  S  A
    470     475     480

1513 AAACCCTTGGATTATGTGGAGATTCACAAGGTCAACAAAGATGGT
   K  P  L  D  Y  V  E  I  H  K  V  N  K  D  G
    485     490     495

1558 GCATTATCATTGCTACCAAAACAGAGAGAGAACAGCGGCAAGCCC
   A  L  S  L  L  P  K  Q  R  E  N  S  G  K  P
    500     505     510

1603 AAGAAGCCCGGGACTCCTGAGAACAATAAGGAGTATGCCAAGGTG
   K  K  P  G  T  P  E  N  N  K  E  Y  A  K  V
    515     520     525

1648 TCCGGGGTCATGGATAACAACATCCTGGTGTTGGTGCCAGATCCA
   S  G  V  M  D  N  N  I  L  V  L  V  P  D  P
    530     535     540

FIG. 10

```
1693 CATGCTAAAAACGTGGCTTGCTTTGAAGAATCAGCCAAAGAGGCC
        H   A   K   N   V   A   C   F   E   E   S   A   K   E   A
                     545                 550                 555
1738 CCACCATCACTTGAACAGAATCAAGCTGAGAAAGCCCTGGCCAAC
        P   P   S   L   E   Q   N   Q   A   E   K   A   L   A   N
                     560                 565                 570
1783 TTCACTGCAACATCAAGCAAGTGCAGGCTCCAGCTGGGTGGTTTG
        F   T   A   T   S   S   K   C   R   L   Q   L   G   G   L
                     575                 580                 585
1828 GATTACCTGGATCCCGCATGTTTTACACACTCCTTTCACTGATAG
        D   Y   L   D   P   A   C   F   T   H   S   F   H   ---
                     590                 595         598
1873 CTTGACTAATGGAATGATTGGTTAAAATGTGATTTTTCTTCAGGT
1918 AACACTACAGAGTACGTGAAATGCTCAAGAATGTAGTCAGACTGA
1963 CACTACTAAAGCTCCCAGCTCCTTTCATGCTCCATTTTTAACCAC
2008 TTGCCTCTTTCTCCAGCAGCTGATTCCAGAACAAATCATTATGTT
2053 TCCTAACTGTGATTTGTAGATTTACTTTTGCTGTTAGTTATAAA
2098 ACTATGTGTTCAATGAAATAAAAGCACACTGCTTAGTATTCTTGA
2143 GGGACAATGCCAATAGGTATATCCTCTGGAAAAGGCTTTCATGAT
2188 TTGGCATGGACAGACGGAAATGAAATTGTCAAAATTGTTTACCA
2233 TAGAAAGATGACAAAAGAAAATTTTCCACATAGGAAAATGCCATG
2278 AAAATTGCTTTTGAAAAACAACTGCATAACCTTTACACTCCTCGT
2323 CCATTTTATTAGGATTACCCAAATATAACCATTTAAAGAAAGAAT
2368 GCATTCCAGAACAAATTGTTTACATAAGTTCCTATACCTTACTGA
2413 CACATTGCTGATATGCAAGTAAGAAAT
```

C-DNA ENCODING HUMAN PROLACTIN RECEPTOR

FIELD OF THE INVENTION

The present invention relates to the isolation and cloning of the cDNA and the development of the human prolactin receptor in a plasmid vector containing the cDNA capable of transforming cell lines that will produce the human prolactin receptor.

BACKGROUND OF THE INVENTION

The anterior pituitary hormone prolactin (PRL) is encoded by a member of the growth hormone/prolactin/placental lactogen gene family. In mammals, it is primarily responsible for the development of the mammary gland and lactation. Prolactin stimulates the expression of milk protein genes by increasing both gene transcription and mRNA half-like.

In addition to the classical effects in the mammary gland, prolactin has been shown to have a number of other actions, all of which are initiated by an interaction with specific high affinity receptors located on the plasma membrane and widely distributed in a number of tissues.

Different biological approaches (cross-linking, immunoprecipitation, or immunoblot with monoclonal antibodies) have shown that the prolactin receptor in many tissues has a relative molecular mass ($M_r$) of approximately 40,000 and is apparently not linked by disulfide bonds to itself or to other subunits. There are reports of larger (70,000-80,000) molecular weight forms of the receptor.

Prolactin receptor levels are differentially regulated depending on the tissue studied. In rat liver, for example, one of the tissues with the highest prolactin binding, receptor levels vary during the estrous cycle, increase during pregnacy, and are markedly stimulated by estrogens. Prolactin plays a major role in the regulation of its own receptor, inducing both up- and down-regulation depending on the concentration and duration of exposure to prolactin.

However, as is true for grown hormone (GH), no means of signal transduction has been identified for prolactin. There are no clear effects of prolactin on cyclic AMP, cyclic GMP, inositol phospholipids, phosphorylation, calcium ions, or ion channels. Neither the GH nor the PRL receptor appear to be a tyrosine kinase.

A better understanding of prolactin receptor structure, regions involved in hormone binding, signal transduction, and possible homology with other hormone receptors would certainly help to shed some light on the mechanism by which prolactin induces its various actions.

Recently, the amino acid sequences of the rabbit and human GH receptors were deduced from their respective cDNA sequences. The authors found no sequence homology of the GH receptor with any other reported protein. Furthermore, the rat PRL receptor was recently purified by Boutin et al. as described in 1988 Cell Vol. 53, 69-77, who also obtained partial amino acid sequence information and cloned and sequence the cDNA. Comparison of the sequence with that of the mammalian growth hormone receptor demonstrated some regions of identity between the two receptors, suggesting the receptors originated from a common ancestor.

It is well known that prolactin plays a major role in the development of the mammary gland and in the induction and maintenance of lactation, via a stimulation of the expression of milk protein genes. The measurement of prolactin receptor levels may be used as a means of predicting the response of a patient with breast cancer, since tumors containing prolactin receptors may be more differentiated and thus less progressed toward a cancerous state. Therefore, the isolation and sequencing of the cDNA and gene encoding the production of human prolactin receptor, as well as its expression in cell lines, would be highly desirable.

SUMMARY OF THE INVENTION

The present invention relates to a synthetic recombinant DNA molecule containing the cDNA sequence of the human prolactin receptor. This synthetic recombinant DNA molecule is a very important genetic engineering tool that can be used for the screening of growth hormone variants, for the development of test kits to measure prolactin receptor levels in human breast and prostate cancer biopsies, for the measurement of "bioactive" forms of prolactin and for the development of drugs to induce stimulation or inhibition of the immune system. The cDNA of the present invention inserted into any one of several plasmids is capable of transformation and replication in various cell-lines such as CHO, COS-7, and S. frugiperda. The procedures through which the PRL receptor cDNA was isolated and cloned are outlined in the following description.

DETAILED DESCRIPTION OF THE INVENTION

Isolation of the Human PRL Receptor cDNA

It has been proven to be extremely difficult to generate enough pure human prolactin receptor using standard purification techniques such as affinity chromatography. Therefore, one suitable alternative is to isolate the human prolactin receptor cDNA by screening a library with a probe based on the rat prolactin receptor cDNA.

The human PRL receptor cDNA is isolated by screening a λ gt10 library prepared from normal human hepatoma Hep G2 and T47-D breast cancer cells. Initially, $1 \times 10^6$ recombinants are screened with the following probe: a complementary RNA of the F3 cDNA of the rat prolactin receptor.

The screening techniques employed correspond to techniques generally employed by those skilled in the technique. One positive recombinant was isolated from the Hep G2 library, which was later used as a probe to rescreen the library. Five additional cDNAs were identified, and by combining two of the six cDNAs, a prolactin receptor cDNA of 2.5 kb was constructed, containing a single open reading frame of 1866 bp. Similar partial length cDNAs were isolated from the T47-D library.

The complete sequence of the human prolactin receptor cDNA is shown in FIG. 1. As can be seen from FIG. 1, the sequence comprises a signal peptide of 24 amino acids followed by a mature protein of 598 amino acid residues. There is a signel transmembrane portion of 24 amino acids in length, based on the hydropathy profile. Several regions of sequence identity between the human growth hormone and prolactin receptors can be found, both in the extracellular and cytoplasmic domains.

A second longer form of the PRL receptor appears to be the predominant species in both the rabbit and human (FIG. 4) in contrast to the shorter form found in rat liver. The rabbit PRL receptor is a 592 amino acid protein highly similar to the extracellular and cytoplasmic domains of the rat prolactin receptor. The cloning of this receptor is described by Edery et al. in 1989, Proc. Natl. Acad. Sci., U.S.A. The rabbit receptor has a much longer cytoplasmic domain than the rat PRL receptor. The human PRL receptor (598 amino acids) has a similar overall structure to the rabbit mammary receptor.

Figure 1A:
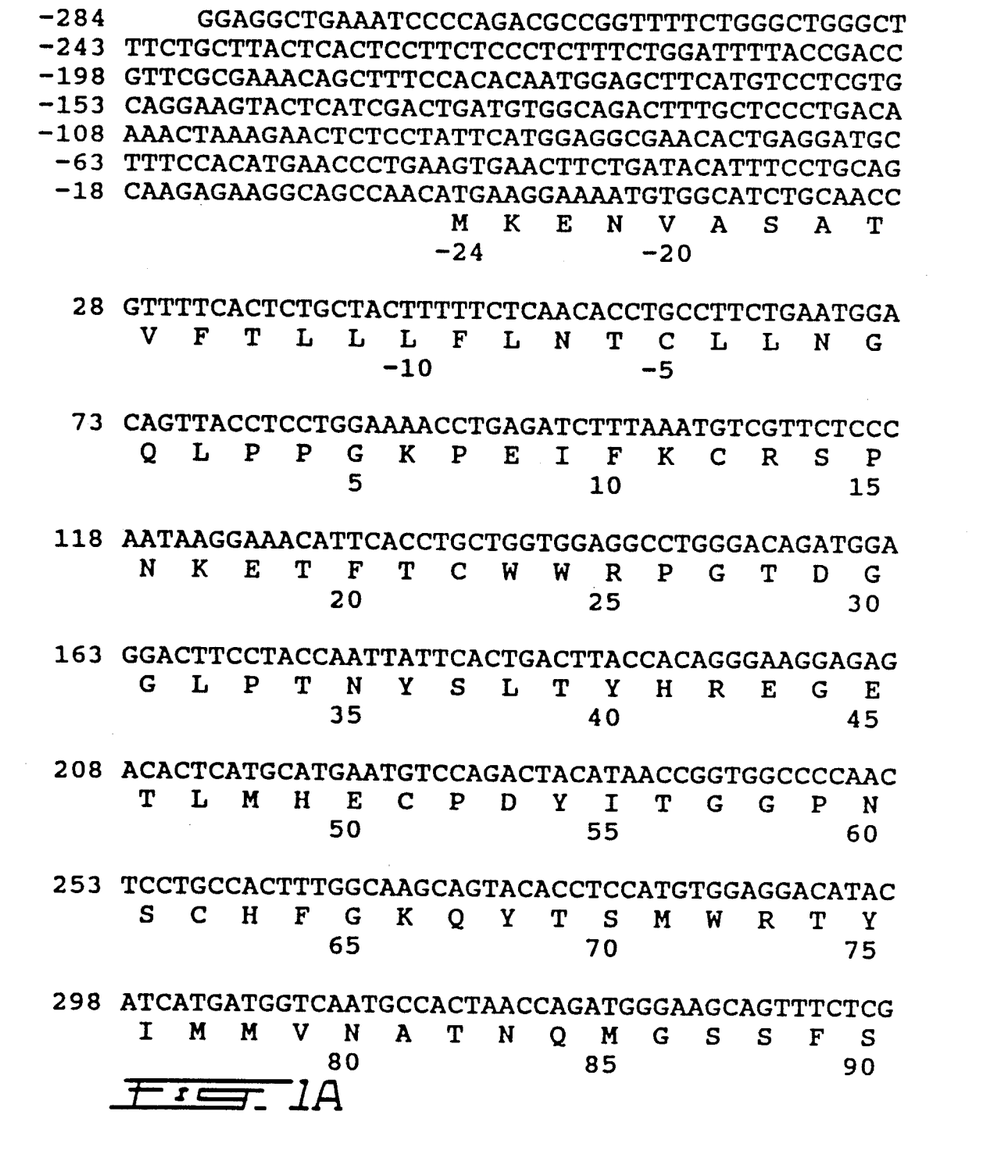
FIG. 1 parts A to E represent the complete sequence of the human prolactin receptor cDNA.
Figure 1B:
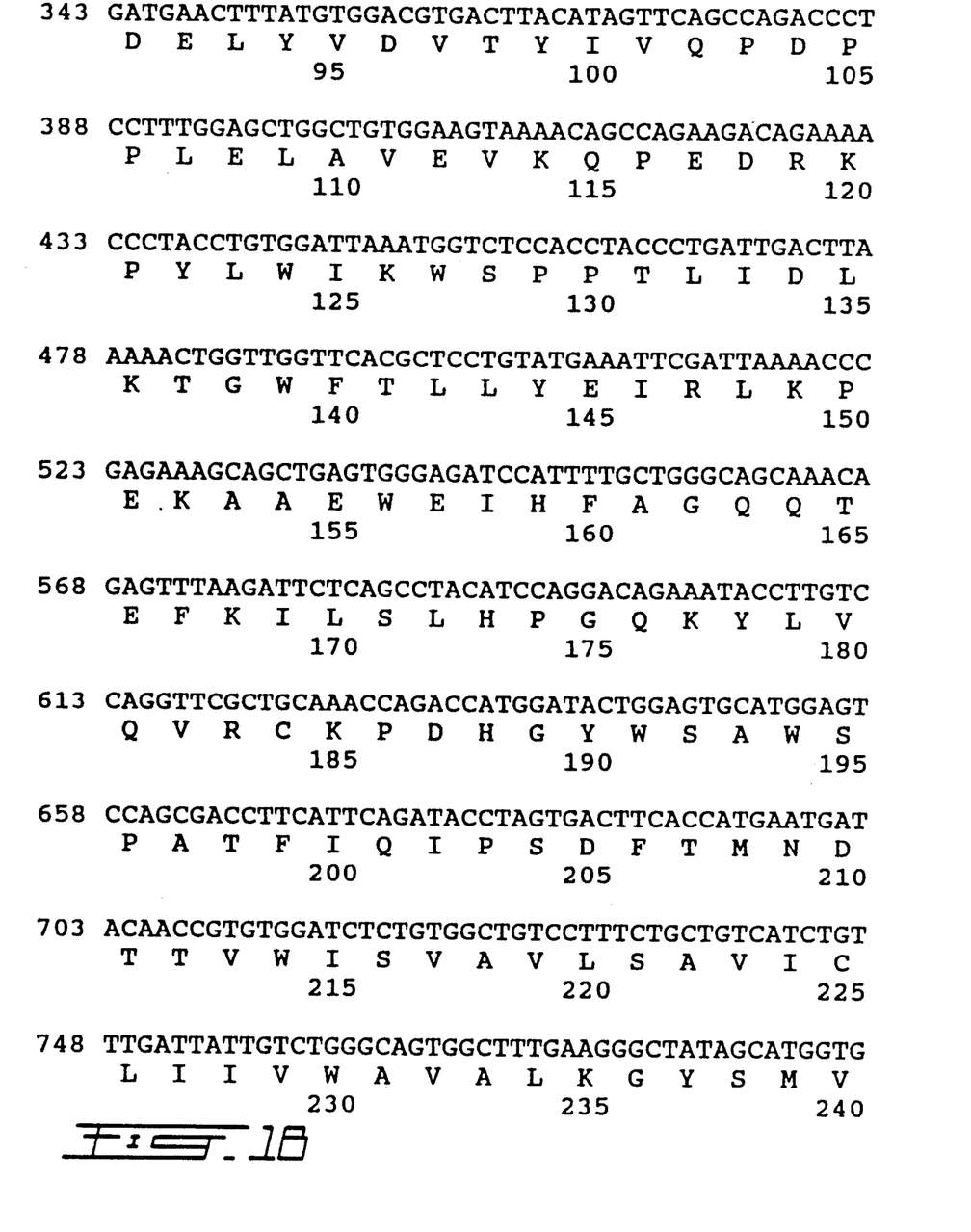
Figure 1C:
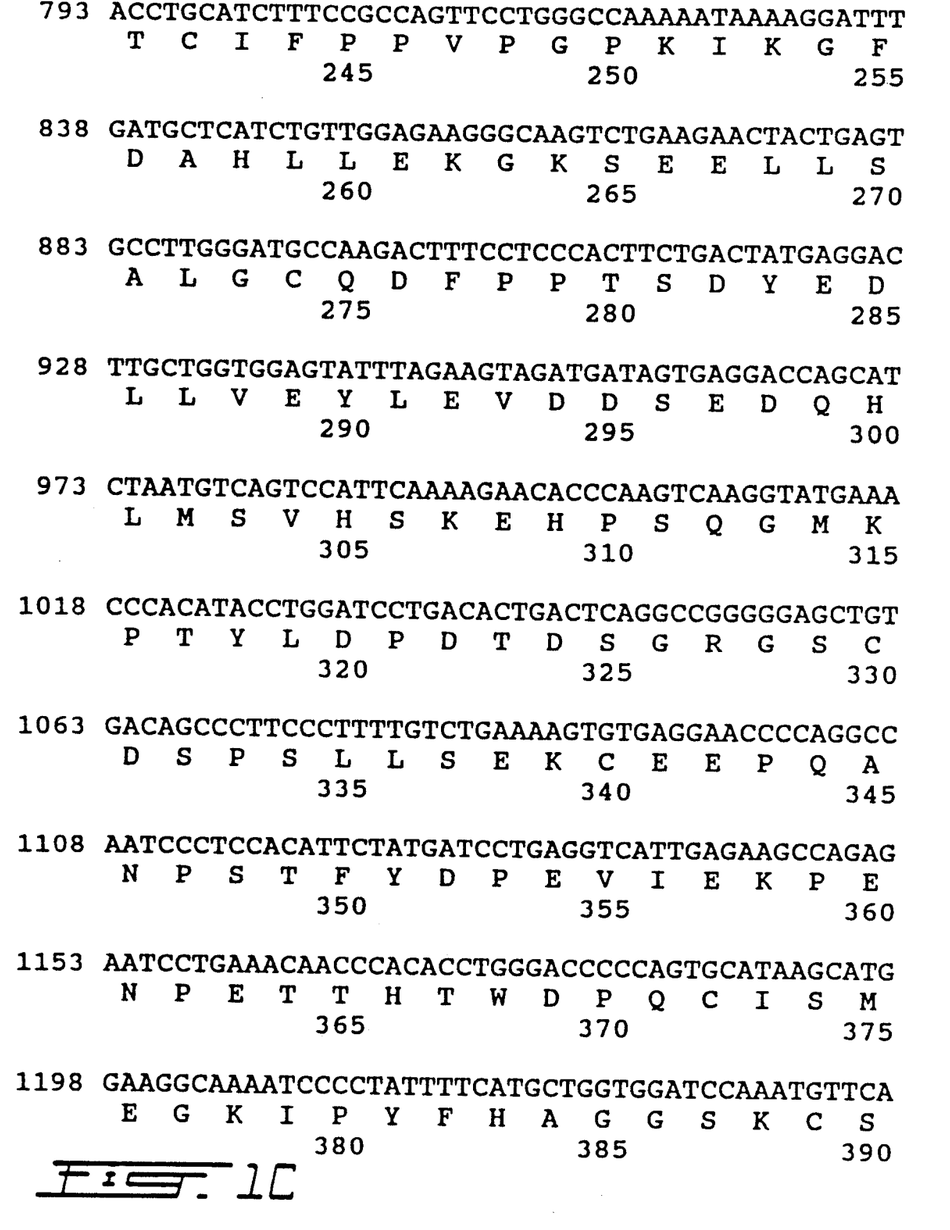
Figure 1D:
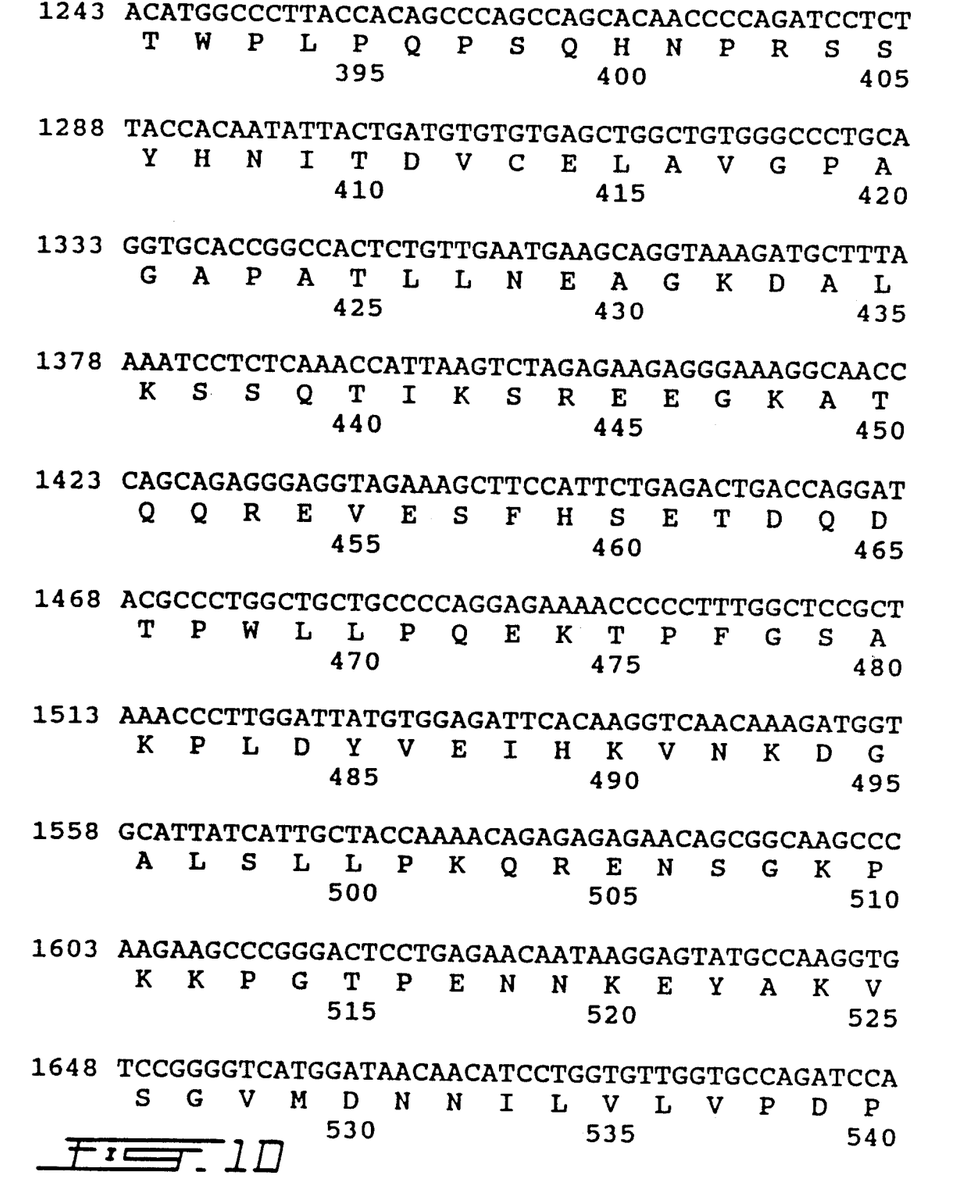
Figure 1E:
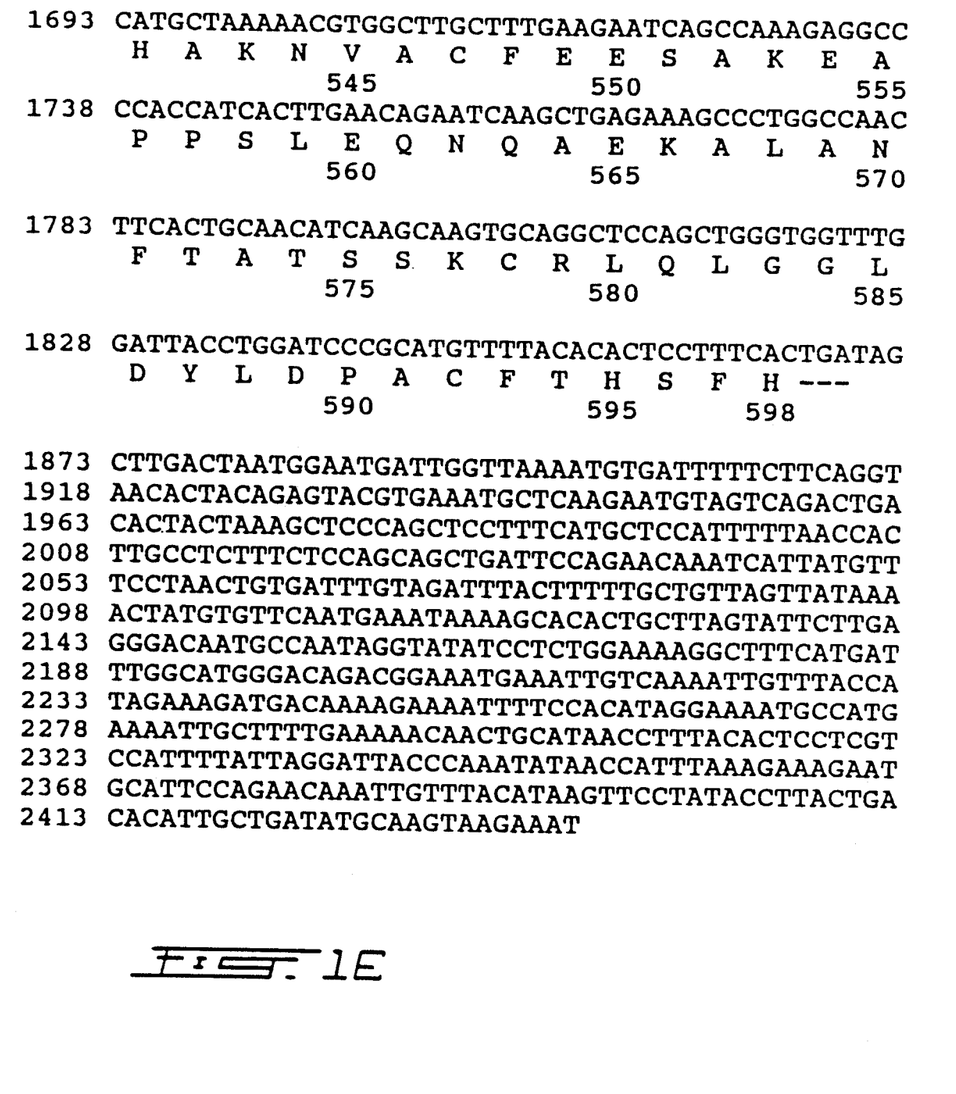
Figure 2:
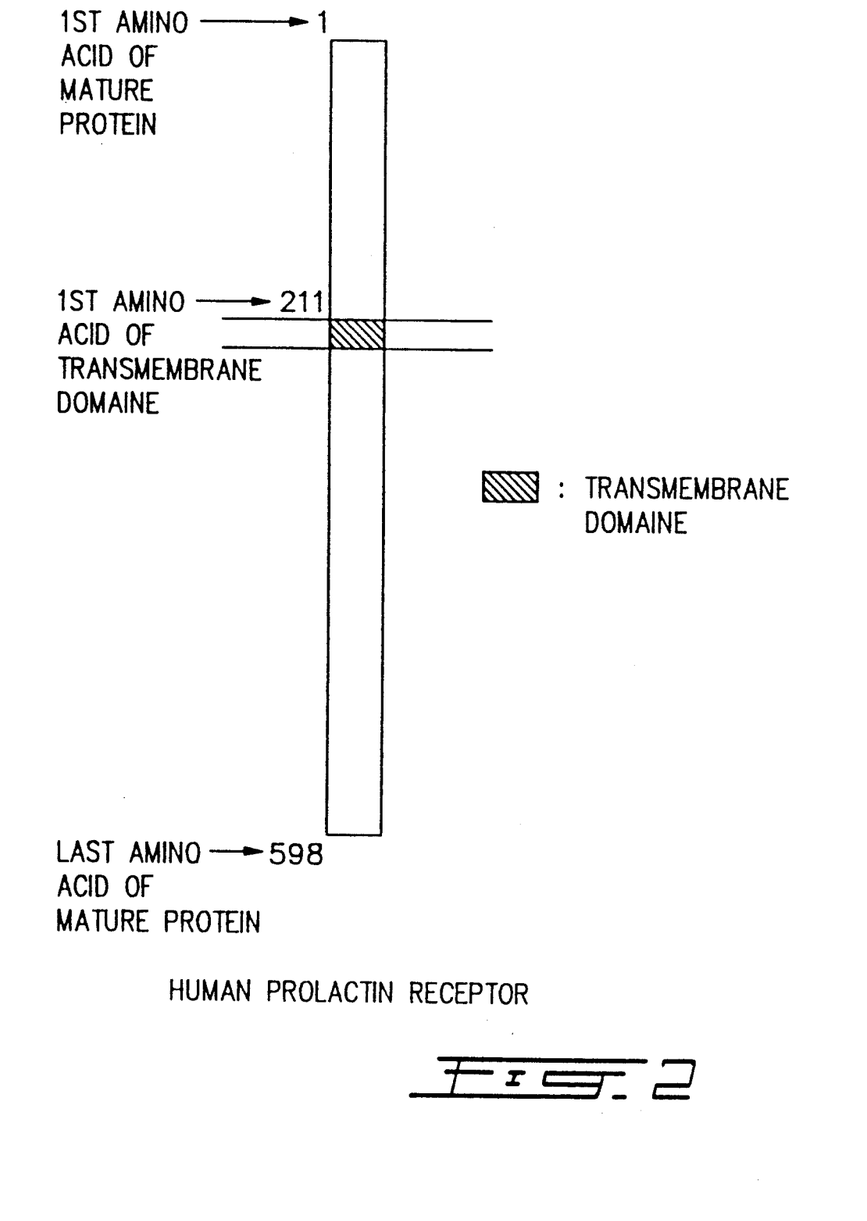
FIG. 2 graphically demonstrates the human prolactin receptor and its insertion orientation in the plasma membrane.
Figure 3:
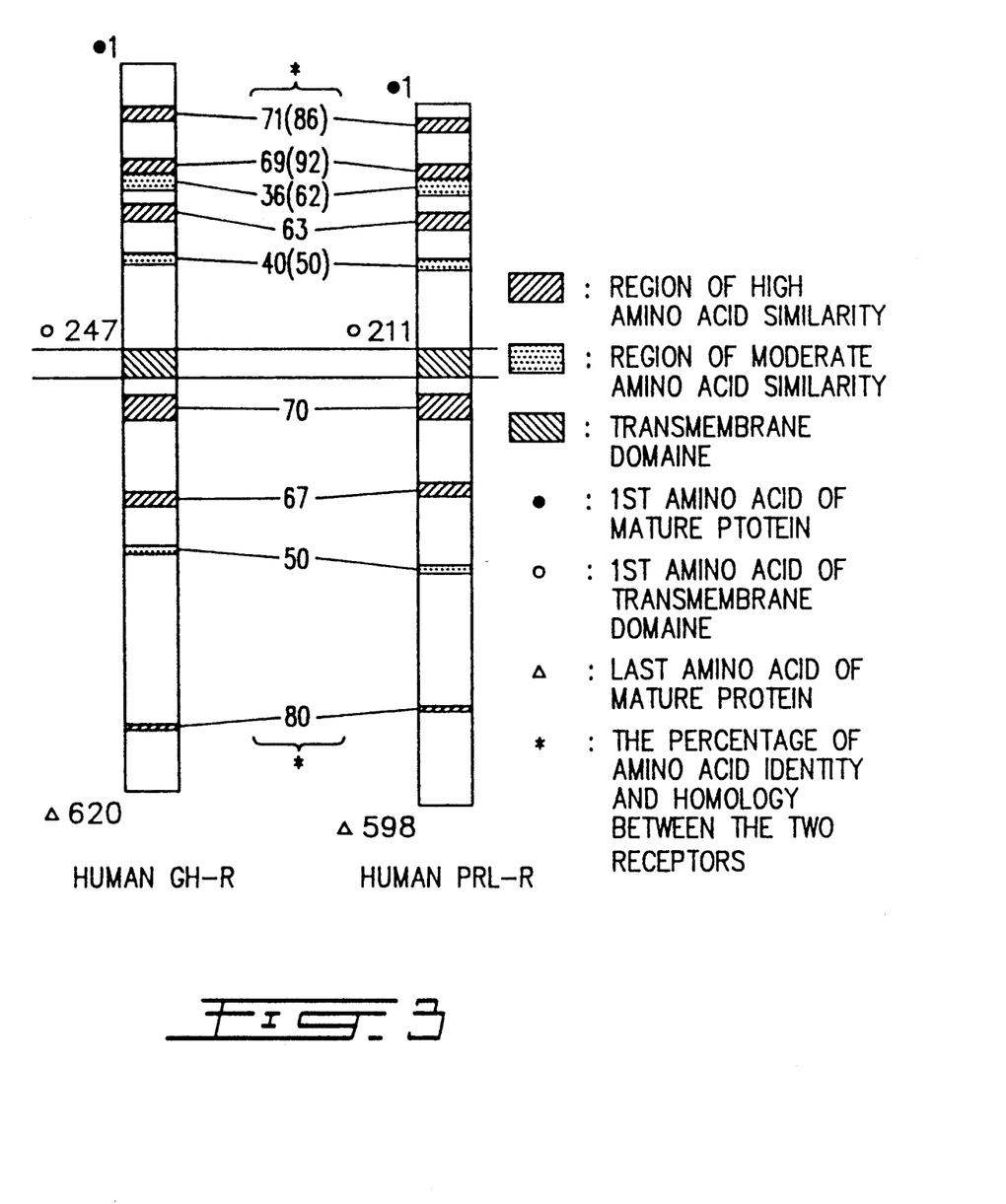
FIG. 3 represents a comparison of the sequences of amino acid identity between the human PRL and growth hormone (GH) receptors.
Figure 4:
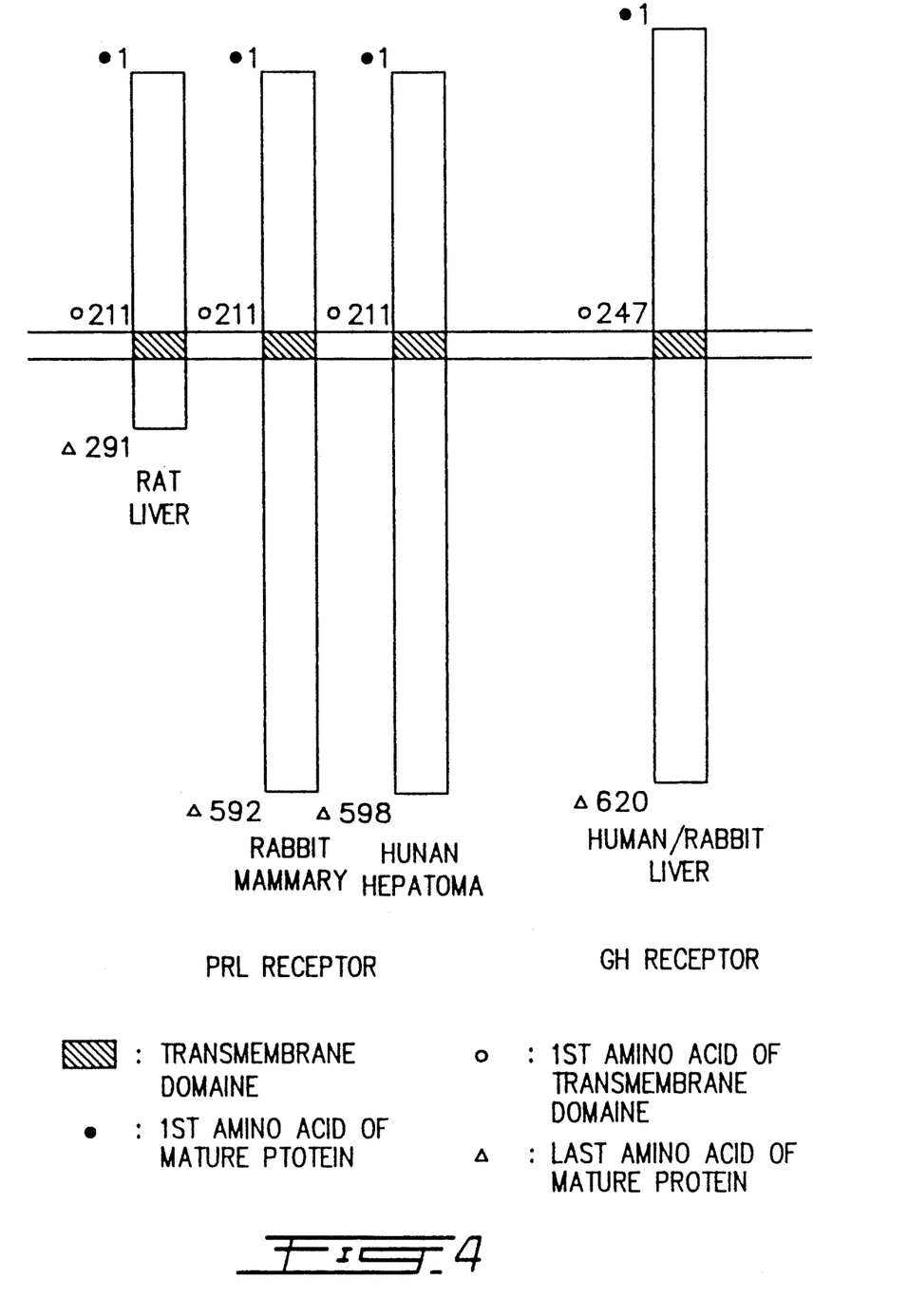
FIG. 4 represents a structural comparison of some prolactin and growth hormone receptors with the human prolactin receptor.

The long form of the PRL receptor is much closer in size to that of the rabbit and human GH receptor which has recently been cloned and sequenced by Leung et al. as described in 1987, Nature 330, 537–543. In addition to the highly conserved sequence just past the transmembrane segment and described by Boutin et al. in 1988, Cell 53:69–77, there are 3 additional regions of a strong sequence identity between the PRL and GH receptors in this extended cytoplasmic domain of both the rabbit and human receptors. Interestingly, this second form of the PRL receptor has been identified in the rat ovary, making it the first species in which both forms of the receptor have been identified. The longer form of the receptor is probably also present in the art mammary gland, and other tissues in which multiple forms of receptor mRNAs have been identified (FIG. 4). Alternative RNA splicing is the probable mechanism responsible for the different forms of the receptor that appear.

Expression of the Human PRL Receptor cDNA

The cDNA encoding the human prolactin receptor may be introduced into various expression vectors containing a bacterial replication of origin, a strong promoter, a polyadenylation signal and an antibiotic resistance marker such as expression vector pECE, pKCR2 and the like. For example, the 2.5 kb cDNA fragment of the prolactin receptor containing the entire open reading frame plus 5' and 3' untranslated sequences can be inserted into the Eco RO site of the plasmid pECE. The recombinant plasmid is verified by restriction endonuclease mapping, and competent bacteria are transformed with the plasmid. Sufficient quantities of purified DNA are prepared (maxiprep).

Transfection of mammalian cells is performed using the calcium phosphate technique. Chinese hamster ovary (CHO), monkey kidney cells (COS-7) or any suitable mammalian cell line grown to about 50% confluence are treated with calcium phosphate to permeate cells, and 10 μg of vector DNA such as pECE-human prolactin receptor cDNA is added. Cells can be used within 2-3 days (transient transfection) if the plasmid is cotransfected with another plasmid conferring neomycin resistance (pSV2 neo), stable transfectants can be isolated after about 4 weeks. Other transfection systems also exits (e.g. baculovirus in insect cells) which results in an overproduction of the receptor protein.

The expressed receptor can be used for screening assays to help select variants of human growth hormone lacking lactogenic activity. Antibodies to the receptor protein (purified from receptor expressed in mammalian or insect cells) or synthetic peptides (prepared from the amino acid sequence) deduced from the cDNA sequence will be used to develop specific assays to measure the receptor levels in cells and tissues (radioimmunoassay, sandwich assay, enzyme immunoassay, immunohistochemistry). Alternatively, mRNA can be detected by in sity localization. Finally, the cDNA sequence comprising the extracellular, hormone binding region can be coupled to a reporter protein that is easily measured (e.g. β-gal) and used in such a way in a soluble system so that the "bioactive" form of prolactin could be measured directly, bypassing the need to use radioisotopes. Such an approach could be applied to any hormone receptor cDNA that has been cloned.

Claims to the invention follow.

We claim:

1. An isolated DNA sequence comprising the cDNA sequence encoding human prolacting receptor.

2. A recombinant DNA molecule containing a DNA sequence comprising the cDNA sequence encoding human prolactin receptor.

3. The recombinant DNA molecule of claim 2, wherein the cDNA sequence encoding human prolactin receptor is inserted at the Eco RI site of a pECE plasmid.

* * * * *